(12) United States Patent
Chen et al.

(10) Patent No.: US 10,161,005 B2
(45) Date of Patent: Dec. 25, 2018

(54) METHOD FOR DETECTING TELOMERASE VIA WASHING-FREE ANCHORED-EXTENSION AND TELOMERIC-BINDING AMPLIFICATION, AND KIT

(71) Applicant: ZHEJIANG JFK BIOLOGICAL TECHNOLOGY CO. LTD., Hangzhou (CN)

(72) Inventors: Ran Chen, Hangzhou (CN); Xiaozheng Jin, Hangzhou (CN)

(73) Assignee: ZHEJIANG JFK BIOLOGICAL TECHNOLOGY CO. LTD., Hangzhou (CN)

( * ) Notice: Subject to any disclaimer, the term of this patent is extended or adjusted under 35 U.S.C. 154(b) by 312 days.

(21) Appl. No.: 14/961,251

(22) Filed: Dec. 7, 2015

(65) Prior Publication Data
US 2016/0168642 A1 Jun. 16, 2016

Related U.S. Application Data

(63) Continuation of application No. PCT/CN2014/078540, filed on May 27, 2014.

(30) Foreign Application Priority Data

Jun. 7, 2013 (CN) .......................... 2013 1 0228271

(51) Int. Cl.
*C12Q 1/68* (2018.01)
*C12Q 1/6883* (2018.01)
(Continued)

(52) U.S. Cl.
CPC ............ *C12Q 1/6883* (2013.01); *C12P 19/34* (2013.01); *C12Q 1/48* (2013.01); *C12Q 1/686* (2013.01); *C12Q 2600/158* (2013.01)

(58) Field of Classification Search
CPC .............. C12Q 1/686; C12Q 2521/113; C12Q 2565/537; C12Q 1/48; C12Q 1/6883; C12Q 2600/158; C12P 19/34
See application file for complete search history.

(56) References Cited

FOREIGN PATENT DOCUMENTS

| CN | 102876792 | 1/2013 |
|---|---|---|
| CN | 103333958 | 10/2013 |

(Continued)

OTHER PUBLICATIONS

International Search Report and Written Opinion issued in the corresponding PCT Application No. PCT/CN2014/078540, dated Aug. 22, 2014, 18 pages.

(Continued)

*Primary Examiner* — Teresa E Strzelecka
(74) *Attorney, Agent, or Firm* — Hamre, Schumann, Mueller & Larson, P.C.

(57) ABSTRACT

Provided is a new method for telomerase amplification—washing-free anchored-extension and telomeric-binding amplification (WATA). The method comprises: utilizing an anchored telomerase primer to conduct telomere TTAGGGG sequence ("G sequence") extension; hybridizing with a template probe having a universal PCR primer sequence and six units of telomere CCCTAA sequence ("C sequence") on the extended G sequence; removing the uncombined template probe via an enzyme digestion reaction; and the template probe combined with the G sequence conducts PCR reaction, the amplification product being a peculiar DNA fragment of a fixed length.

6 Claims, 1 Drawing Sheet
Specification includes a Sequence Listing.

(51) Int. Cl.
*C12Q 1/48* (2006.01)
*C12P 19/34* (2006.01)
*C12Q 1/686* (2018.01)
*C07H 21/02* (2006.01)

(56) References Cited

FOREIGN PATENT DOCUMENTS

| | | |
|---|---|---|
| CN | 103343119 | 10/2013 |
| EP | 1108789 | 6/2001 |

OTHER PUBLICATIONS

Lin et al., "Development in Mammalian Telomerase Activity Research", Heilongjiang Animal Science and Veterinary Medicine, No. 7, vol. 31, pp. 40-42, Jul. 31, 2012. (Cited in ISR and Written Opinion; English abstract provided).

Ohyashiki et al., "Cytological Detection of Telomerase Activity Using an in Situ Telomeric Repeat Amplification Protocol Assay", Cancer Research, vol. 57, pp. 2100-2103, Jun. 1, 1997.

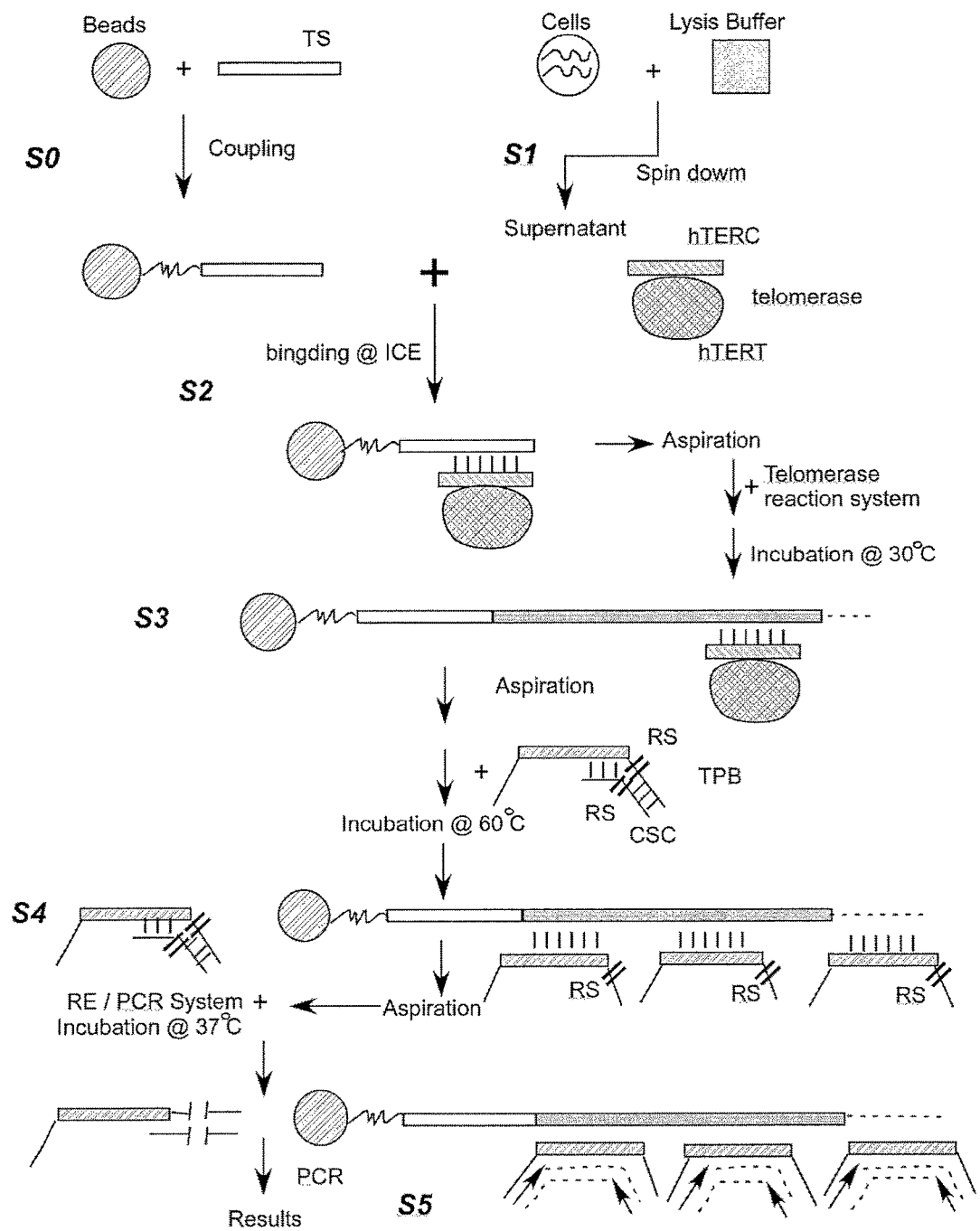

SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: telomerase primer sequence

<400> SEQUENCE: 1
tccgtcgagc agagttaggg ttag    24

<210> SEQ ID NO 2
<211> LENGTH: 78
<212> TYPE: DNA
<213> ORGANISM: Artificial Sequence
<220> FEATURE:
<223> OTHER INFORMATION: template probe

<400> SEQUENCE: 2
ccgtcaccct ggatgctgta ggatccctaa ccctaaccct aaccctaacc ctaaccctaa    60
ggatcgctcg cggctctt    78

```
<210> SEQ ID NO 3
<211> LENGTH: 19
<212> TYPE: DNA
<213> ORGANISM: Artificial Sequence
<220> FEATURE:
<223> OTHER INFORMATION: inhibitory probe sequence

<400> SEQUENCE: 3
tagggttagg gatcctaca                                               19

<210> SEQ ID NO 4
<211> LENGTH: 22
<212> TYPE: DNA
<213> ORGANISM: Artificial Sequence
<220> FEATURE:
<223> OTHER INFORMATION: upstream primer

<400> SEQUENCE: 4
ccgtcaccct ggatgctgta gg                                           22

<210> SEQ ID NO 5
<211> LENGTH: 20
<212> TYPE: DNA
<213> ORGANISM: Artificial Sequence
<220> FEATURE:
<223> OTHER INFORMATION: downstream primer

<400> SEQUENCE: 5
aagagccgcg agcgatcctt                                              20

<210> SEQ ID NO 6
<211> LENGTH: 11
<212> TYPE: RNA
<213> ORGANISM: Homo Sapiens
<220> FEATURE:
<223> OTHER INFORMATION: template sequence of telomerase RNA

<400> SEQUENCE: 6
cuaacccuaa c                                                       11
```

METHOD FOR DETECTING TELOMERASE VIA WASHING-FREE ANCHORED-EXTENSION AND TELOMERIC-BINDING AMPLIFICATION, AND KIT

TECHNICAL FIELD

The present application relates to a method and kit for detecting the telomerase by washing-free, anchored-extension and telomeric-binding amplification (WATA).

BACKGROUND

Telomerase is a special reverse transcriptase, which is a ribonucleoprotein (RNP) complex formed of RNA in association with a protein, and comprises 3 main components: a telomerase RNA (TERC) template, a telomerase catalytic subunit (Telomerase Reverse Transcriptase, TERT), and a telomerase-associated protein (TLP). TERC is a template for use in an extension reaction by the telomerase, which has about 450 bases including a template sequence 5'-CUAAC-CCUAAC-3' (SEQ ID NO: 6). TERT is a catalytic subunit of the telomerase, and TLP is the regulatory unit of the telomerase. Telomerase mainly functions to synthesize and extend the telomere-TTAGGG-repeat sequence (G sequence) by using a 3' terminus of the telomeric DNA at the end of the chromosome as a primer and using its own RNA as a template, so as to compensate the telomeric DNA sequence lost during cell division. In some particular tissue cells, for example, germ cells, embryonic stem cells, hematopoietic stem cells, peripheral blood lymphocytes, hair, skin, and endometrial cells, and other highly dividing tissue cells, activated telomerase is expressed at a low level. However, no telomerase activity is detected in a normal mature somatic cell, and aging and death of the cells are caused by the gradually shortening of the telomere. Very few somatic cells may escape from the programmed aging by accidently activating the telomerase. However, the prolonged survival of these cells may provide opportunities for build-up of additional genetic damages, causing progressive tumor development, that is, cancerization. Therefore, telomerase reactivation is a critical step in the transition of somatic cells to tumor cells, i.e., cancerization. Until now, it is found that a majority of the malignant tumor cells are telomerase positive (>85%), and the telomerase positive rate in the peri-tumorous and normal tissues are very low (<5%). Accordingly, telomerase is a generally recognized tumor marker of high specificity. It is anticipated that the detection of telomerase may be developed into a powerful tool in the detection and molecular diagnostics of cancers. The specimen for telomerase detection may be derived from cultured cells, surgically removed tissues, needle aspiration biopsies, hydrothorax, ascites, bladder or pancreatic duct washings, secretions taken by cotton swabs, sputum, and urine.

The existing methods for detecting the telomerase activity include: 1. non-PCR based detection methods, wherein the product resulted from the telomerase catalyzed extension reaction is directly analyzed and determined by isotope, fluorescent, and chemiluminescent assay. Due to the limited sensitivity, they are substantially replaced by the detection methods based on PCR amplification at present; 2. conventional PCR-based detection methods of the telomerase activity, including Telomeric Repeats Amplification Protocols (TRAPs) and methods derived therefrom, in which the amplification products are a series of DNA fragments of different lengths; and 3. non-TRAP PCR-based detection methods, including Premature Termination of telomere extension-PCR (PTEP) and Anchored-Extension and Telomeric Complements Amplification (AETCA), in which the amplification product is a specific DNA fragment of a fixed length.

The conventional TRAP method requires the troublesome polyacrylamide gel electrophoresis and staining steps. Later to this, improvements have been made by many researchers, in particular, the introduction of internal standard enables the accurate semi-quantitative determination with the aid of some analytical instruments. However, the improvements are made only with respect to the detection means post PCR, the core TRAP-PCR reaction used is unchanged, and thus the following inherent defects of the TRAP method cannot be overcome:

(1) The amplification efficiency is low. Because in the TRAP method, the product resulting from the telomerase catalyzed extension reaction is directly used as a template for PCR, and the obtained PCR products are a series of lanes that are from dozens of by to hundreds of by in length. The uncertainty of the amplification products causes great limitation to the amplification efficiency, thereby reducing the sensitivity.

(2) A specificity-related problem exists. The uncertainty of the TRAP amplification products leads to a problem that the analysis of the results trends to be interfered by non-specific PCR amplification.

(3) The repeatability/stability is poor. Because for the TRAP method, a cell lysate is directly added into the PCR system and the cell lysate generally contains numerous ingredients inhibiting the PCR reaction, the failure of the entire detection may generally be caused.

(4) Limitations on the sensitivity are caused by the system. The cell lysate may be added to the detection system in a volume that is not larger than 4% of the total volume, which limits the detection sensitivity.

(5) The applicability is limited. The method is not applicable to the detection of the inhibition effect on telomerase, since PCR is linked to the telomerase catalyzed extension reaction, and the telomerase inhibitor has a strong inhibition on PCR.

(6) The real-time fluorescent quantitative PCR is difficult to be performed. Due to the interference from the non-specific PCR amplification, SYBR staining is not applicable, and the TaqMan probe method is not applicable since the probe region is overlapped with the downstream primer region.

The PTEP method was reported by CHEN Ran, et al in 2003 and a patent (ZL00127583.6) has been granted thereto in China in the same year. The principle of the method is that the PCR primer plays a function by complementary binding of its 3' end to a template, and the mismatch in a middle part of the chain does not hinder the initiation of the PCR reaction. In this method, a specially constructed 159 bp DNA is introduced, and the telomerase primer TS is completely complementary to two ends of the 159 bp DNA except for two bases at the 3' end. By adding no dTTP, the telomerase catalyzed extension reaction is restrictedly terminated in a unit, to obtain an early terminated extension product TS+AGGG, after that, dTTP and a Taq enzyme are added to the system, and the TS+AGGG is used as a starting primer to initiate the amplification of the 159 bp DNA. After 2 PCR cycles, because the completely complementary sequence of TS is integrated into a new product, TS is used as a PCR primer for amplifying the new product. The amplification product is a specific fragment of the 159 bp DNA, and can be appropriately assayed by various conventional analysis methods. The main improvement of the method over the TRAP method is that in contrast to the uncertain amplification products of varying sizes in the TRAP method, the amplification product is changed to a specific amplified fragment. However, because the telomerase catalyzed extension reaction is linked to PCR and no improvements are made with respect to the inhibition of the cell lysate on PCR, the repeatability/stability is not good enough. Moreover, the process is troublesome because the reagents (dTTP and the Taq enzyme) need to be supplemented tubewise during the reaction.

The AETCA method was invented by CHEN Ran et al in 2012. In the method, an anchored telomerase primer is used for extension of the telomeric G sequence, and another template probe having a pair of universal PCR primer sequences and 6 units of telomeric C complementary sequences is hybridized and bound to the anchored telomeric G sequence. The unbound template probe is removed by repeatedly washing, and the template probe bound to the anchored telomeric G sequence is amplified in subsequent PCR reaction. The product is a specific DNA fragment of a fixed length. In the method, the PCR inhibiting materials may be removed by the repeated washing steps, and the template probe is bound to the anchored telomeric G sequence as multiple copies, such that the PCR template is enriched, and the overall sensitivity of the method is improved. However, the repeated washing steps are troublesome, and the binding of the template probe to the target G sequence has a high requirement on temperature control and is influenced by the variation in ambient temperature. Where the room temperature is too low, non-specific binding may occur, leading to false positive results and thus causing the fluctuation and inconsistency of the results. In the present invention, considerable improvements are made on the AETCA method by removing the template probe unbound to the G sequence by introducing an inhibitory probe mediated enzymatic cleavage reaction to replace the washing steps.

SUMMARY

An object of the present invention is to provide a method and a kit for a simple, rapid, and efficient detection of telomerase activity.

The following technical solutions are employed in the present invention:

A method for detecting telomerase activity by washing-free, anchored-extension and telomeric-binding amplification (WATA) is provided. The method comprises: adding a cell lysate supernatant of a test sample to a PCR tube fixed with a telomerase primer; placing the PCR tube on ice to bind telomerase to the primer; after the supernatant being aspirated off, adding a telomerase reaction system composed of a template probe, an inhibitory probe, a buffer and dNTP; incubating the mixture at 30-37° C. to perform the telomeric G sequence extension reaction, and then the mixture being incubated at 55-65° C. to perform the hybridization reaction; after aspiration off of liquid, adding a PCR reaction solution containing a restriction endonuclease and PCR primers, incubated at 37° C. for 10 min, and then carrying out the PCR reaction; and subjecting the PCR reaction product to fluorescent quantification or analysis by agarose gel electrophoresis.

The telomerase primer sequence is:

(SEQ ID NO: 1)
5'-TCCGTCGAGCAGA*GTTAGGGTTAG*-3', wherein the highlighted italicized part of the sequence is a sequence that is complementarily bound to the template region of the telomerase TERC, and the 5' end thereof is fixed to the wall of the PCR tube, magnetic beads or other solid matrices that can adsorb and bind nucleic acid; the telomerase primer TS can be fixed by a conventional method in the art, and the matrices for fixing the telomerase primer TS may be a plastic centrifuge tube, magnetic beads, gel particles or other solid matrices that can adsorb and bind nucleic acid.

The template probe (in which the two ends are the PCR primer recognition sites, the middle part is a complementary sequence (the C sequence) of n units of telomeric repeats $(TTAGGG)_n$ (the G sequence), and a restriction endonuclease cleavage site is added between the C sequence and the PCR primer recognition site) is:

(SEQ ID NO: 2)
5'-CCGTCACCCTGGATGCTGTA*GGATCCC*TAACCCTACCCTAACCCTA
ACCCTAACCCTAAGGATCGCTCGCGGCTCTT-3', wherein the shaded part is a complementary C sequence of 6 units of G sequences $(TTAGGG)_6$, the highlighted italicized part of the sequence is a BamHI recognition site, and the boxed part is a region binding to the inhibitory sequence, the two terminal sequences are PCR recognition sites of a universal PCR primer pair 5'-

(SEQ ID NO: 4)
5'-CCGTCACCCTGGATGCTGTAGG-3'
and (SEQ ID NO: 5)
5'-AAGAGC C G C G A GCG A TCCTT-3'.

The inhibitory probe sequence is (SEQ ID NO: 3)
5'-TAGGGTTAG*GGATCC*TACA-3', wherein the highlighted italicized part of the sequence is a BamHI recognition site.

The PCR primer sequences include
an upstream primer:

(SEQ ID NO: 4)
5'-CCGTCACCCTGGATGCTGTAGG-3', and
a downstream primer:

(SEQ ID NO: 5)
5'-AAGAGCCGCGAGCGATCCTT-3'.

Specifically, the method includes the following steps:

(1) A telomerase primer is synthesized, and fixed to a PCR reaction tube to obtain an anchor PCR tube.

Preferably, the anchor PCR tube fixed with the telomerase primer is prepared as follows: 50 μl of TBST buffer containing 5 pmol biotinylated telomerase primer is added into a 0.2 ml thin-wall PCR tube coated with streptavidin and stood at room temperature for 1 hr. The liquid in the tube is aspirated off, and 100 μl of TBST buffer is added, the obtained mixture is pipetted, and liquid is aspirated off. The tube is repeatedly washed 3 times, and then the liquid is aspirated off. 100 μl of TE buffer is added and the liquid in the tube is then aspirated off. The tube is sealed and stored at −20° C. for later use.

(2) The template probe and the inhibitory probe are synthesized respectively.

(3) The template probe and the inhibitory probe are complexd to form a double-stranded DNA, and designated as dsTU.

The process is specifically as follows: the template probe and the inhibitory probe are dissolved in a TE buffer respectively, and equal moles of the template probe and the inhibitory probe are mixed, the mixture is stood at 60° C. for 10 min and then at 37° C. for 10 min, followed by being cooled to the room temperature to obtain the dsTU. The dsTU has an intact BamHI recognition site, and thus can be cleaved by BamHI.

The products obtained in above steps may be prepared in a large quantity before the telomerase activity is detected, and stored at −20° C. for later use.

(4) A lysis buffer is added to the test sample, the mixture is repeatedly pipetted, transferred to a centrifuge tube, placed on ice for 10 min, and centrifuged at 4° C. The supernatant is removed and used as the lysate supernatant. The lysis buffer is conventionally known in the art, it contains a surfactant (e.g. Tween 20, NP-40, CHAPS, or the like), and is used for cell or tissue lysis, with the telomerase activity being retained.

The test sample may be obtained from tissues or cells, or from clinical specimens, such as sputum and blood.

When the test sample is sputum derived, the lysate supernatant may be prepared as follows: 1-5 ml of sputum and 5-10 ml of pretreatment buffer are mixed and agitated at 37° C. for 10 min, and centrifuged for 10 min at 4° C. and 5000 rpm. The supernatant is discarded, 200 μl of lysis buffer is added to the pellet and the mixture is repeatedly pipetted, transferred to a 1.5 ml centrifuge tube, placed on ice for 20 min, and centrifuged at 4° C. and 15000 rpm for 20 min. The supernatant is removed and used as the lysate supernatant. The pretreatment buffer has a composition of PBS+0.1% (w/vol) DTT.

When the test sample is cell derived, the lysate supernatant may be prepared as follows: the cells are cultured in a 24-well plate, and the media is aspirated off. 200 μl of lysis buffer is added, the mixture is repeatedly pipetted, transferred to a 1.5 ml centrifuge tube, placed on ice for 10 min, and centrifuged at 4° C. and 15000 rpm for 20 min. The supernatant is removed and used as the lysate supernatant.

When the test sample is tissue derived, the lysate supernatant may be prepared as follows: about 0.1 cm$^3$ of tissue mass is placed in a 1.5 ml centrifuge tube, 200 μl of lysis buffer is added, the mixture is repeatedly pipetted, transferred to a 1.5 ml centrifuge tube, placed on ice for 10 min, and centrifuged at 4° C. and 15000 rpm for 20 min. The supernatant is removed and used as the lysate supernatant.

Preferably, the lysis buffer has a composition of: 1 mmol/L MgCl$_2$, 1 mmol/L EGTA-Na, 1% (vol/vol) NP-40 (which is a mild surfactant, and can generally destroy the cell membrane while has a weak destruction on the nuclear membrane with a concentration of 1%), 0.25 mmol/L sodium deoxycholate, 150 mmol/L NaCl, 10% (vol/vol) glycerol, 5 mmol/L 2-mercaptoethanol, 0.1 mmol/L AEBSF, and 10 mmol/LTris-HCl (pH7.5) as the solvent.

(5) The lysate supernatant is added to the anchor PCR tube, the tube is gently agitated, the mixture in the tube is placed on ice for 30 min (to bind the telomerase molecules in the lysate supernatant to the fixed telomerase primer in the reaction tube), and the liquid is aspirated off A telomerase reaction solution formulated with a buffer (telomerase reaction buffer), dNTP, and dsTU is added, and incubated at 30-37° C. for 30-60 min (to carry out the telomeric G sequence extension reaction) and then at 55-65° C. for 15-30 min (to melt dsTU, and complex the template probe T restored to be single-stranded to the extended telomeric G sequence). The liquid in the tube is aspirated off (to remove the material inhibiting and interfering with the enzymatic cleavage and PCR reaction). A RE/PCR reaction solution formulated with a buffer (RE/PCR reaction buffer), dNTP, a Taq enzyme, a PCR primer, SYBR green I or a TaqMan probe, and BamHI is added. Then the following procedures are performed on a PCR instrument: enzymatic cleavage at 37° C. for 5-15 min (where the remaining trace amount of dsTU is cleaved, the template probe T bound to the telomeric G sequence is not enzymatically cleaved because the intactness of the BamHI recognition site is destroyed, and the integrated enzymatic cleavage can not only prevent the PCR reaction from interference by the template probe T that is not hybridized and bound to the telomere extension sequence, but also prevent the cross contamination caused by the spread of small amount of PCR product aerosol, thus ensuring the specificity and success rate of the PCR reaction), predenaturization at 92-95° C. for 2-5 min, and then 35 cycles of: 92-95° C. for 3-30 sec and 55-65° C. for 20-60 sec. The amplification product is analyzed by fluorescent quantitative assay. The buffer is one conventionally used in the PCR reaction.

In practical detection, a blank lysis buffer is used as a negative control. Using the treatment and analysis in Steps (4)-(5), the result is determined to be positive if the Ct value of the sample is less than that of the blank lysis buffer and the absolute vale of the difference therebetween is greater than or equal to 1.

Preferably, the telomerase reaction solution in Step (5) (telomerase reaction buffer+0.06 mmol/L dNTP+1 nmol/L dsTU) has a composition of: 0.06 mmol/L dNTP, 1 nmol/L dsTU, 1.5 mmol/L MgCl$_2$, 63 mmol/L KCl, 1 mmol/L EGTA-Na, 0.1 mg/ml BSA, 0.05% (vol/vol) Tween20, and 20 mmol/L Tris-HCl (pH 8.0) as the solvent.

Preferably, the RE/PCR reaction solution in Step (5) (RE/PCR buffer+dNTP+Taq enzyme+PCR primer+SYBR green I (or TaqMan probe)+BamHI) has a composition of 0.2 mmol/L dNTP, 1 U/50 μl Taq enzyme, 0.2 μmol/L PCR primers, 0.4×SYBR Green I, 2 U/50 μl BamHI, 50 mmol/L KCl, 1.5 mmol/L MgCl$_2$, 0.05% (vol/vol) Tween 20, and 10 mmol/L Tris-HCl (pH 9.0) as the solvent.

The present invention further relates to a kit for detecting the telomerase activity by washing-free, anchored-extension and telomeric-binding amplification (WATA), which substantially comprises an anchor PCR tube fixed with a telomerase primer, a template probe, an inhibitory probe, PCR primers, a telomerase reaction buffer, a RE/PCR reaction buffer, a Taq enzyme and a BamHI enzyme. In addition to the above main reagents, the kit may further comprise dNTP, SYBR Green I, or a TaqMan probe, as desired by those skilled in the art.

The telomerase primer sequence is:

(SEQ ID NO: 1)
5'-TCCGTCGAGCAGA*GTTAGGGTTAG*-3'.

The template probe sequence is:

(SEQ ID NO: 2)
5'-CCGTCACCCTGGATGCTGTA*GGATCCC*TAACCCTAACCCTAACCCTA
ACCCTAACCCTAAGGATCGCTCGCGGCTCTT-3'.

The inhibitory probe sequence is:

(SEQ ID NO: 3)
5'-TAGGGTTAC*GGATCC*TACA-3'.

The PCR primer sequences include (SEQ ID NO: 4)
5'-CCGTCACCCTGGATGCTGTAGG-3',
and (SEQ ID NO: 5)
5'-AAGAGCCGCGAGCGATCCTT-3'.

The telomerase reaction buffer has a composition of: 1.5 mmol/L MgCl$_2$, 63 mmol/L KCl, 1 mmol/L EGTA-Na, 0.1 mg/ml BSA, 0.05% Tween 20, and 20 mmol/L Tris-HCl (pH 8.0) as the solvent.

The RE/PCR reaction buffer has a composition of: 50 mmol/L KCl, 1.5 mmol/L MgCl$_2$, 0.05% Tween 20, and 10 mmol/L Tris-HCl (pH 9.0) as the solvent.

The kit may further comprises a cell lysis buffer having a composition of: 1 mmol/L MgCl$_2$, 1 mmol/L EGTA-Na, 1% NP-40, 0.25 mmol/L sodium deoxycholate, 150 mmol/L NaCl, 10% (vol/vol) glycerol, 5 mmol/L 2-mercaptoethanol, 0.1 mmol/L AEBSF, and 10 mmol/L Tris-HCl (pH 7.5) as the solvent.

In the TRAP method, the telomere extension product is amplified. According to the present invention, the benefits of the AETCA method is remained, that is, a template probe complementarily binding to the telomeric sequence rather than a telomere extension sequence is used as a PCR template. The template probe may be bound as multiple copies to a long telomere extension sequence synthesized in the presence of telomerase. As such, although the telomere extension sequence varies in length, the template probe can still be amplified efficiently to a fixed length with a high efficiency, thereby overcoming the defect of low efficiency caused by varying lengths in the TRAP method. In the present method, the repeated washing steps in the AETCA method are not required, such that the operation is simplified and the consistency is increased. Moreover, in the method, the telomerase molecule is bound to the anchored telomerase primer through low temperature adsorption first, and then the PCR inhibiting material is removed by aspirating off and replacing the liquid, thereby improving the PCR amplification efficiency.

Compared with the TRAP method, the method according to the present invention increases the number of the PCR template, thus increasing the detection sensitivity. The increase in the number of the template is estimated as follows:

Given that the telomere extension product generally has a distribution ranging from 36 bp (6 units) to 354 bp (59 units) at an increment of 6 bp, the number of the template probe that may be bound to the telomere extension product is estimated as follows:

a. in the range of 36 bp-66 bp, a total of 6 telomere extension products may exist at an increment of 6 bp, each binding 1 template probe;

in the range of 72 bp-102 bp, a total of 6 telomere extension products may exist at an increment of 6 bp, each binding 2 template probes;

. . .

in the range of 324 bp-354 bp, a total of 6 telomere extension products may exist at an increment of 6 bp, each binding 9 template probes; and b. the total number of the template probe is:
(1+2+3+4+5+6+7+8+9)×6=270

Therefore, it can be inferred that the sensitivity of the present method is 270 times of that of the TRAP method.

Because only in the case that there are more than 6 units of single-stranded TTAGGG telomeric DNA sequences, the intactness of the BamHI recognition site in the template region is destroyed and the BamHI recognition site in the PCR amplification product is kept intact. If the WATA system is contaminated with a small amount of amplification product, the amplification product is cleaved by the BamHI present in the system. Therefore, another advantage of the method according to the present invention is that the false-positive cross-contamination caused by the amplification product may be restricted to some extent.

The present invention has the benefits that the method according to the present invention is simple and feasible in operation, has an increased sensitivity and specificity in detection of the telomerase activity, and is suitable for use in the detection of cells or tissues derived from various sources including clinical specimens such as sputum.

BRIEF DESCRIPTION OF THE DRAWINGS

FIG. 1 is a schematic process flow chart of a method according to the present invention, which includes:

Step S0: a telomerase primer (TS) is fixed;

Step S1: the cells are lysed to obtain a lysate supernatant containing telomerase molecules;

Step S2: the lysate supernatant is placed on ice to adsorb and bind the telomerase molecules to the TS;

Step S3: after aspiration off of liquid, the telomerase reaction system is added, and subjected to the telomere extension reaction and then to the hybridization reaction, such that a template probe is bound to the telomere extension product;

Step S4: after aspiration off of liquid, a RE/PCR system is added, and incubated at 37° C. before the PCR reaction procedure, so as to cleave the remaining template probe, where the template probe bound to the telomere extension product is kept intact because the enzymatically cleavable site is single-stranded and cannot be cleaved; and Step S5: the PCR procedure is carried out and the template probe is amplified, indicating the telomerase activity.

TS, telomerase primer; TPB, template probe; CSC, inhibitory probe; RS, restriction site.

DETAILED DESCRIPTION OF THE INVENTION

The present invention is described in further detail with reference to specific examples. However, the protection scope of the present invention is not limited thereto.

Example 1: Removal of the Interference with PCR from a Small Amount of dsTU by a WATA System Integrated with the BamHI Enzyme (1) Synthesis of the primer and probe sequences as follows:

The sequence of the telomerase primer S is:

5'-TCCGTCGAGCAGA*GTTAGGGTTAG*-3'.

The sequence of the telomerase primer S is:

(SEQ ID NO: 1)
5'-TCCGTCGAGCAGA*TTAGGGTTAG*-3'.

The sequence of the template probe T is:

(SEQ ID NO: 2)
5'-CCGTCACCCTGGATGCTGTA***GGATCCCTAACCCTAACCCTAACCCTA
ACCCTAACCCTA***AGGATCGCTCGCGGCTCTT-3'.

The sequence of the inhibitory probe U is:

(SEQ ID NO: 3)
5'-TAGGGTTAG*GGATCC*TACA-3'.

The sequences of the PCR primers are:

(SEQ ID NO: 4)
5'-CCGTCACCCTGGATGCTGTAGG-3',
and (SEQ ID NO: 5)
5'-AAGAGCCGCGAGCGATCCTT-3'.

(2) Preparation of anchor PCR tubes fixed with the telomerase primer S:

50 μl of TBST buffer containing 5 pmol biotinylated telomerase primer S was charged to a 0.2 ml Thin-wall PCR tube coated with streptavidin and stood at room temperature for 1 hr. The liquid in the tube was aspirated off, and 100 μl of the TBST buffer was added, pipetted, and aspirated off. The tube was repeatedly washed 3 times, and then aspirated off. 100 μl of TE buffer was added and the liquid in the tube is then aspirated off. The tube was sealed and stored at −20° C. for later use.

(3) Compositions of the lysis buffer and the reaction solution

The lysis buffer had a composition of: 1 mmol/L $MgCl_2$, 1 mmol/L EGTA-Na, 1% (vol/vol) NP-40, 0.25 mmol/L sodium deoxycholate, 150 mmol/L NaCl, 10% (vol/vol) glycerol, 5 mmol/L 2-mercaptoethanol, 0.1 mmol/L AEBSF, and 10 mmol/L Tris-HCl (pH7.5) as the solvent.

The telomerase reaction solution (the reaction solution T) had a composition of: 0.06 mmol/L dNTP, 1 nmol/L dsTU, 1.5 mmol/L $MgCl_2$, 63 mmol/L KCl, 1 mmol/L EGTA-Na, 0.1 mg/ml BSA, 0.05% Tween 20, and 20 mmol/L Tris-HCl (pH 8.0) as the solvent.

The RE/PCR reaction solution had a composition of: 0.2 mmol/L dNTP, 1 U/50 μl of Taq enzyme, 0.2 μmol/L PCR primers, 0.4×SYBR Green I, 2 U/50 μl BamHI, 50 mmol/L KCl, 1.5 mmol/L $MgCl_2$, 0.05% Tween 20, and 10 mmol/L Tris-HCl (pH 9.0) as the solvent.

The conventional BamHI free PCR reaction solution had a composition of: 0.2 mmol/L dNTP, 1 U/50 μl Taq enzyme, 0.2 pmol/L PCR primers, 0.4×SYBR Green I, 50 mmol/L KCl, 1.5 mmol/L $MgCl_2$, 0.05% Tween 20, and 10 mmol/L Tris-HCl (pH 9.0) as the solvent.

Human lung cancer cell line A549 (commercially available from ATCC, US) was cultured at a density of 10000 cells/well in 8 wells in a 24-well plate. After overnight culture, the media was aspirated off. 200 μl of the lysis buffer T was added per well, repeatedly pipetted, transferred to 8 centrifuge tubes of 1.5 ml respectively, placed on ice for 10 min, and centrifuged at 4° C. and 15000 rpm for 10 min. The supernatant was removed and used as the lysate supernatant.

50 μl of the lysate supernatant was added to 8 reaction tubes of 0.2 ml fixed with the telomerase primer respectively, 4 of which were then added with 1 nmol/L dsTU respectively, and the other 4 of which were added with $ddH_2O$ control in a volume equal to that of dsTU. After incubation at 30° C. for 30 min and then at 60° C. for 30 min, the liquid was aspirate off. The BamHI free conventional PCR reaction solution was added to 4 tubes (2 of which contained dsTU, and the other 2 of which contained the $ddH_2O$ control, the same below), and the RE/PCR reaction solution containing BamHI was added to the other 4 tubes. The amplification was carried out on a fluorescent quantitative PCR instrument at 37° C. for 10 min, and 94° C. for 3 min, followed by 40 cycles of 94° C. for 5 sec and 63° C. for 30 sec, and the amplification product was analyzed by SYBR green I fluorescent quantitative assay. The result is shown below.

| Reaction system | Ct-dsTU | Ct-$ddH_2O$ |
|---|---|---|
| Conventional PCR | 20.72 | 29.38 |
| Conventional PCR | 20.53 | 29.49 |
| RE/PCR | 29.21 | 29.55 |
| RE/PCR | 29.05 | 29.42 |

It can be seen that the Ct value (resulting from the primer dimer) of the $ddH_2O$ control in the 2 systems is greater than 29. As to the conventional PCR, the Ct value of the dsTU tube is less than 21, which is far below the value of the control, suggesting that after the lysate supernatant containing 1 nmol/L dsTU in the reaction tube is aspirated off, the remaining trace amount of dsTU is considerably amplified. The Ct value of the RE/PCR dsTU tube is greater than 29, which is comparable with the value of the control, suggesting that the background arising from the amplification of the remaining small amount of dsTU can be effectively controlled by the RE/PCR system through cleavage.

Example 2: Removal of Interference Resulting from Contamination with a Small Amount of PCR Product by a WATA System Integrated with the BamHI Enzyme The primer and probe sequences, the reaction tube, the lysis buffer T, the reaction solution T, the conventional PCR reaction solution and the RE/PCR reaction solution were the same as those in Example 1.

The A549 cells and the preparation of the lysate supernatant were the same as those in Example 1. 50 μl of the lysate supernatant was added to 8 reaction tubes of 0.2 ml fixed with the telomerase primer respectively, 4 of which were then added with the amplification product at a dilution of $10^{-7}$ respectively, and the other 4 of which were added with equal volume of $ddH_2O$ control. After incubation at 30° C. for 30 min and then at 60° C. for 30 min, the liquid was aspirate off. The BamHI free conventional PCR reaction system was added to 4 tubes (2 of which contained the amplification product, and the other 2 of which contained $ddH_2O$ control, the same below), and the RE/PCR reaction system containing BamHI was added to the other 4 tubes.

The amplification was carried out on a fluorescent quantitative PCR instrument at 37° C. for 10 min and 94° C. for 3 min, followed by 40 cycles of 94° C. for 5 sec and 63° C. for 30 sec, and the amplification product was analyzed by SYBR green I fluorescent quantitative assay. The result is shown below.

| Reaction system | Ct-Product | Ct-ddH$_2$O |
| --- | --- | --- |
| Conventional PCR | 15.39 | 29.54 |
| Conventional PCR | 15.11 | 29.81 |
| RE/PCR | 29.15 | 29.67 |
| RE/PCR | 29.03 | 29.50 |

It can be seen that the Ct value (resulting from the primer dimer) of the ddH$_2$O control in the 2 systems is greater than 29. As to the conventional PCR, the Ct value of the amplification product tube is less than 16, which is far below the value of the control, suggesting that the amplification product at a dilution of $10^{-7}$ can cause contamination to the conventional PCR reaction system, which results in serious false positive results. The Ct value of the RE/PCR amplification product tube is greater than 29, which is comparable with the value of the control, suggesting that the false positive results arising from the contamination with the small amount of amplification product can be effectively controlled by the RE/PCR reaction system through cleavage.

Example 3: Detection of the Telomerase Activity in Human Lung Cancer A549 Cells by the WATA Method The primer and probe sequences, the reaction tube, the lysis buffer T, the reaction solution T, and the RE/PCR reaction solution were the same as those in Example 1.

The detection method was carried out as follows:

(1) The A549 cells were cultured in a 24-well plate (at a density of about 10-10000 cells/well), and then the media was aspirated off. 200 μl of the lysis buffer T was added per well, repeatedly pipetted, transferred to a 1.5 ml centrifuge tube, placed on ice for 20 min, and centrifuged at 4° C. and 15000 rpm for 20 min. The supernatant was removed and used as the lysate supernatant.

(2) 50 μl of the lysate supernatant was added to the anchor PCR tube, placed on ice for 30 min, and aspirated off, and then 50 μl of the reaction solution T containing 1 nmol/L dsTU was added, and incubated at 30° C. for 30 min and then at 60° C. for 30 min.

(3) After aspiration off of the liquid, 50 μl of the RE/PCR reaction system (containing the PCR buffer, 0.2 μmol/L PCR primers, 0.2 mmol/L dNTP, 1 U Taq enzyme, and 2 U BamHI) was added. The amplification was carried out on a PCR instrument at 37° C. for 10 min and 94° C. for 3 min, followed by 40 cycles of 94° C. for 5 sec and 63° C. for 30 sec, and the amplification product was analyzed by SYBR green I fluorescent quantitative assay.

(4) The lysis buffer and the thermally deactivated (at 80° C. for 10 min) lysate supernatant of 1000 cells were used as the negative control, and in Steps 2)-3) in place of the lysate supernatant.

(5) When the Ct value was ≤28, a positive result was determined, and when the Ct value was >28, a negative result was determined.

The result is shown below.

| Sample | Ct | Result |
| --- | --- | --- |
| Lysis buffer | 29.55 | Negative |
| 10 cells | 27.76 | Positive |
| 100 cells | 24.19 | Positive |
| 1000 cells | 20.83 | Positive |
| 10000 cells | 17.21 | Positive |
| Thermally deactivated lysate supernatant | 29.38 | Negative |

It can be seen that the telomerase activity in 10-10000 A549 cells can be detected by the WATA method.

Example 4: Stability of Reaction Tubes Fixed with the Telomerase Primer Prepared in Large Quantity The primer and probe sequences, the reaction tube, the lysis buffer T, the reaction solution T, and the RE/PCR reaction solution were the same as those in Example 1.

(1) 24 reaction tubes were divided into 6 groups, each having 4 tubes. After sealing, the tubes were stored at 37° C. for 1, 2, 3, 4, 5, and 6 days, and recorded as Groups 1, 2, 3, 4, 5, and 6.

(2) The lysate supernatant (2×1 ml) of the A549 cells was prepared following the method in Example 1, where 1 ml was placed on ice and ready for use as a positive control; and the other 1 ml was thermally deactivated (at 80° C. for 10 min) and used as a negative control.

(3) The operations were as described in Steps 2) and 3) in Example 3, each group of the reaction tubes included 2 positive controls, and 2 negative controls.

(4) When the Ct value was ≤28, a positive result was determined, and when the Ct value was >28, a negative result was determined.

The result is shown below.

| Group | Ct-Positive control 1 | Ct-Positive control 2 | Ct-Negative control 1 | Ct-Negative control 2 |
| --- | --- | --- | --- | --- |
| 1 | 17.28 | 17.43 | 29.14 | 29.23 |
| 2 | 17.52 | 17.39 | 29.26 | 29.38 |
| 3 | 17.33 | 17.45 | 29.41 | 29.29 |
| 4 | 17.75 | 17.54 | 29.32 | 29.46 |
| 5 | 24.79 | 21.93 | 29.66 | 29.31 |
| 6 | 27.50 | 28.25 | 29.81 | 29.65 |

It can be seen that after storage at 37° C. for 1-4 days, the reaction tubes fixed with the telomerase primer prepared in large quantity substantially have no influence on the detection results of the telomerase activity, but have a serious influence on the detection results after storage at 37° C. for 5 or more days.

Example 5: Detection of the Telomerase Activity in Human Squamous Cell Carcinoma Cell Line A431 by the WATA Method The primer and probe sequences, the reaction tube, the lysis buffer T, the reaction solution T, and the RE/PCR reaction solution were the same as those in Example 1.

The detection method was as follows.

The A431 cells were cultured in a 24-well plate (at a density of about 10-10000 cells/well), and then the media was aspirated off. 200 μl of the lysis buffer T was added per well, repeatedly pipetted, transferred to a 1.5 ml centrifuge tube, placed on ice for 20 min, and centrifuged at 4° C. and 15000 rpm for 20 min. The supernatant was removed and used as the lysate supernatant. The following operations were the same as those in Example 3. When the Ct value was ≤28, a positive result was determined, and when the Ct value was >28, a negative result was determined.

The results are shown below.

| Sample | Ct | Result |
|---|---|---|
| Lysis buffer | 29.82 | Negative |
| 10 cells | 27.66 | Positive |
| 100 cells | 24.91 | Positive |
| 1000 cells | 21.26 | Positive |
| 10000 cells | 17.68 | Positive |
| Thermally sterilized lysate supernatant | 29.53 | Negative |

It can be seen that the telomerase activity in 10-10000 A431 cells can be detected by the WATA method.

Example 6: WATA Detection Kit

A kit of 8 Tests had a composition as shown below.

| Component | Function | Packing specification |
|---|---|---|
| 1) Concentrated pretreatment buffer | Pretreatment of the sample, and collection, enrichment, and washing of the cells 50-fold diluted with ddH$_2$O before use | 1 × 1.7 ml |
| 2) Lysis buffer T | Lysis of cells Direct use | 1 × 1.7 ml |
| 3) Reaction solution T | Telomeric G sequence extension reaction and hybridization and binding of the template probe Direct use | 1 × 0.45 ml |
| 4) RE/PCR reaction solution | Enzymatic cleavage and PCR proliferation Direct use | 1 × 0.45 ml |
| 5) Negative control | Thermally deactivated lysate supernatant of 1000 A549 cells Direct use | 1 × 0.12 ml |
| 6) Positive control | Lysate supernatant of 1000 freshly frozen A549 cells Direct use | 1 × 0.12 ml |
| 7) Reaction tube | Fixed with telomerase primer Direct use | 1 × 8 |
| 8) Membrane seal | Sealing the reaction tube Direct use | 3 |
| 9) Instruction | Operation instructions and notices | 1 |

The pretreatment buffer had a composition of: 50×PBS+50 g/L DTT, and had a composition of 1×PBS+1 g/L DTT after 50-fold dilution. The composition of 1×PBS was NaCl 137 mM, KCl 2.7 mM, Na$_2$HPO$_4$ 10 mM, KH$_2$PO$_4$ 1.8 mM, and distilled water as the solvent.

The primer sequence, the lysis buffer T, the reaction solution T, and the RE/PCR reaction solution were the same as those in Example 1.

The operation steps were carried out as follows:

(1) The kit was removed from a frozen storage environment, thawed at room temperature, and temporarily stored at 4° C.

(2) The concentrated pretreatment buffer was 50-fold diluted with 83 ml ddH$_2$O, to give a pretreatment buffer that was temporarily stored at 4° C.

(3) A sample was collected, which might be cultured cells and tissues, or sputum, whole blood (supplemented with an anticoagulant), and urine.

The amount of the sample was recommended to be 10-10$^6$ cultured cells, about 0.1 cm$^3$ tissue mass, about 2 ml sputum, about 0.5 ml whole blood, and about 10 ml urine.

The sample was pretreated as follows. The cells cultured in suspension were collected by centrifugation, and then re-suspended in 10 ml of the pretreatment buffer. The tissue mass was soaked in 10 ml of the pretreatment buffer, and chopped. The sputum was agitated with 10 ml of the pretreatment buffer at 37° C. for about 10 min until the sputum was completely dissolved. 10 ml of the pretreatment buffer was directly added to the whole blood. After centrifugation of the urine, the pellet was re-suspended in 10 ml of the pretreatment buffer. The materials obtained above were all further centrifuged, the supernatant was discarded, and the pellet was carried on next step.

(4) The lysis buffer T was added to the pellet in an amount of 200 μl/sample, repeatedly pipetted, transferred to a 1.5 ml centrifuge tube, placed on ice for 20 min, and centrifuged at 4° C. and 15000 rpm for 20 min. The supernatant was removed and used as the lysate supernatant.

(5) 50 μl of the lysate supernatant was added to the anchor PCR tube, placed on ice for 30 min, and aspirated off. 50 μl of the reaction solution T containing 1 nmol/L dsTU was added and incubated at 30° C. for 30 min and then at 60° C. for 30 min (6) The liquid was aspirated off, and then 50 μl of the RE/PCR reaction system (containing the PCR buffer, 0.2 μmol/L PCR primers, 0.2 mmol/L dNTP, 1 U Taq enzyme, and 2 U BamHI) was added. The amplification was carried out on a PCR instrument at 37° C. for 10 min and then 94° C. for 3 min, followed by 35 cycles of 94° C. for 5 sec and 63° C. for 30 sec, and the amplification product was analyzed by SYBR green I fluorescent quantitative assay.

(7) A negative control and a positive control were set in place of the lysate supernatant, and used in Steps 5)-6).

(8) When the Ct value was ≤28, a positive result was determined, and when the Ct value was >28, a negative result was determined.

Example 6: Detection of the Telomerase Activity in Human Embryonic Kidney Cell Line 293T with the WATA Detection Kit for Telomerase Activity The 293T cells (commercially available from ATCC, US) were cultured in a 24-well plate (at a density of about 1-10$^6$ cells/well). The kit and operation steps were as described in Example 5. The lysate supernatant of 1000 cells was thermally deactivated as described in Example 3.

The result is shown below.

| Sample/Control | Ct | Results |
|---|---|---|
| 1 cells | 29.10 | Negative |
| 10 cells | 27.03 | Positive |
| 100 cells | 23.46 | Positive |
| 10$^3$ cells | 20.18 | Positive |
| 10$^4$ cells | 16.79 | Positive |
| 10$^5$ cells | 14.35 | Positive |
| 10$^6$ cells | 14.82 | Positive |
| Negative control | 29.67 | Negative |
| Positive control | 20.44 | Positive |

It can be seen that the telomerase activity in 10-10$^6$ 293 T cells can be detected by the WATA kit. However, when the cell number in the sample reaches to or exceed $10^5$, the Ct value does not decline obviously, suggesting that the amplification limiting factor varies from the telomeric G sequence extension to the template probe, that is, the template probe is completely adsorbed and bound. Therefore, although a higher telomerase activity leads to more telomeric G sequence extension, the number of the PCR template is not increased.

Example 7: Detection of the Telomerase Activity in Human Cervical Cancer Cell Line HeLa with the WATA Detection Kit for Telomerase Activity The Hela cells (commercially available from ATCC, US) were cultured in a 24-well plate (at a density of about $10$-$10^5$ cells/well). The kit and operation steps were as described in Example 5. The lysate supernatant of 1000 cells was thermally deactivated as described in Example 3.

The result is shown below.

| Sample/Control | Ct | Results |
| --- | --- | --- |
| 10 cells | 26.88 | Positive |
| 100 cells | 23.37 | Positive |
| $10^3$ cells | 20.09 | Positive |
| $10^4$ cells | 16.55 | Positive |
| $10^5$ cells | 14.44 | Positive |
| Negative control | 29.59 | Negative |
| Positive control | 20.32 | Positive |
| Thermally deactivated lysate supernatant | 29.66 | Negative |

It can be seen that the telomerase activity in $10$-$10^6$ Hela cells can be detected by the WATA kit, and in the range, the higher the cell number is, the lower the Ct value is, suggesting that the WATA detection for telomerase activity is of great value in quantitative detection.

Example 8: Detection of the Telomerase Activity in Human Breast Cancer Cell Line MCF-7 with the WATA Detection Kit for Telomerase Activity The MCF-7 cells (commercially available from ATCC, US) were cultured in a 24-well plate (at a density of about $10$-$10^5$ cells/well). The kit and operation steps were as described in Example 5. The lysate supernatant of 1000 cells was thermally deactivated as described in Example 3.

The result is shown below.

| Sample/Control | Ct | Results |
| --- | --- | --- |
| 10 cells | 27.92 | Positive |
| 100 cells | 24.43 | Positive |
| $10^3$ cells | 21.27 | Positive |
| $10^4$ cells | 17.88 | Positive |
| $10^5$ cells | 15.29 | Positive |
| Negative control | 29.33 | Negative |
| Positive control | 20.47 | Positive |
| Thermally deactivated lysate supernatant | 29.73 | Negative |

It can be seen that the telomerase activity in $10$-$10^5$ MCF-7 cells can be detected by the WATA kit, and in the range, the higher the cell number is, the lower the Ct value is, suggesting that the WATA detection for telomerase activity is of great value in quantitative detection.

Example 9: Detection of the Telomerase Activity in Sputum Specimen from Lung Cancer Patient with the WATA Detection Kit for Telomerase Activity 20 lung cancer patients were in stage I as diagnosed by needle biopsy of tissues, and have not receive an operation. The sputum was freshly collected in the morning.

The kit and operation steps were as described in Example 5.

Among the 20 lung cancer patients, 16 were detected to be telomerase positive, and 4 were telomerase negative. 2 normal person (who had sputum due to smoking, and were healthy by recently physical examination) control were detected to be telomerase negative.

| Sample/Control | Ct | Results |
| --- | --- | --- |
| Negative control | 29.68 | Negative |
| Positive control | 20.84 | Positive |
| Lung cancer patient JFK-ZJL-201 | 16.33 | Positive |
| Lung cancer patient JFK-ZJL-202 | 19.58 | Positive |
| Lung cancer patient JFK-ZJL-203 | 26.54 | Positive |
| Lung cancer patient JFK-ZJL-204 | 18.29 | Positive |
| Lung cancer patient JFK-ZJL-205 | 30.43 | Negative |
| Lung cancer patient JFK-ZJL-206 | 31.76 | Negative |
| Lung cancer patient JFK-ZJL-207 | 24.99 | Positive |
| Lung cancer patient JFK-ZJL-208 | 27.86 | Positive |
| Lung cancer patient JFK-ZJL-209 | 19.19 | Positive |
| Lung cancer patient JFK-ZJL-210 | 16.93 | Positive |
| Lung cancer patient JFK-ZJL-211 | 17.40 | Positive |
| Lung cancer patient JFK-ZJL-212 | 26.62 | Positive |
| Lung cancer patient JFK-ZJL-213 | 21.52 | Positive |
| Lung cancer patient JFK-ZJL-214 | 28.74 | Negative |
| Lung cancer patient JFK-ZJL-215 | 18.47 | Positive |
| Lung cancer patient JFK-ZJL-216 | 20.78 | Positive |
| Lung cancer patient JFK-ZJL-217 | 29.85 | Negative |
| Lung cancer patient JFK-ZJL-218 | 27.22 | Positive |
| Lung cancer patient JFK-ZJL-219 | 26.59 | Positive |
| Lung cancer patient JFK-ZJL-220 | 20.55 | Positive |
| Normal person JFK-ZJN-001 | 28.96 | Negative |
| Normal person JFK-ZJN-002 | 29.75 | Negative |

It can be seen that the telomerase activity in fresh sputum from most of the lung cancer patients can be detected by the WATA method.

Example 10: Detection of the Telomerase Activity in Surgically Removed Cervical Cancer Tissues with the WATA Detection Kit for Telomerase Activity The surgically removed cervical cancer tissues from 10 cervical cancer patients were frozen at −80° C. About 30 mg frozen cervical cancer tissue was clipped by sterilized ophthalmic scissors. 10 ml of the pretreatment buffer was added, and centrifuged. The supernatant was discarded. 200 µl of the lysis buffer T was added to the pellet, and stood in an ice bath for 30 min. The following operations were as described in Example 5. The kit was as shown in Example 5.

The cervical cancer tissues from the 10 cervical cancer patients are all telomerase positive as detected by WATA.

| Sample/Control | Ct | Results |
| --- | --- | --- |
| Negative control | 29.77 | Negative |
| Positive control | 20.53 | Positive |
| Cervical cancer patient JFK-ZJC-001 | 20.47 | Positive |
| Cervical cancer patient JFK-ZJC-002 | 15.62 | Positive |
| Cervical cancer patient JFK-ZJC-003 | 22.78 | Positive |
| Cervical cancer patient JFK-ZJC-004 | 19.91 | Positive |

| Sample/Control | Ct | Results |
|---|---|---|
| Cervical cancer patient JFK-ZJC-005 | 21.35 | Negative |
| Cervical cancer patient JFK-ZJC-006 | 24.88 | Negative |
| Cervical cancer patient JFK-ZJC-007 | 17.18 | Positive |
| Cervical cancer patient JFK-ZJC-008 | 20.26 | Positive |
| Cervical cancer patient JFK-ZJC-009 | 18.71 | Positive |
| Cervical cancer patient JFK-ZJC-010 | 17.55 | Positive |

It can be seen that the telomerase activity in surgically removed frozen cancer tissues from the cervical cancer patients can be detected by the WATA method.

Example 11: Detection of the Telomerase Activity in ALT+ Lung Cancer Cell Line (SK-LU-1 Cells) with the WATA Detection Kit for Telomerase Activity ALT (alternative lengthening of telomere) is a mechanism by which the telomeric DNA length is extended and maintained in the telomerase negative cancer cells. SK-LU-1 (commercially available from ATCC, US), a known ALT+ cell, was cultured in a 24-well plate (at a density of about $10-10^5$ cells/well). The kit and operation steps were as described in Example 5. The lysate supernatant of 1000 SK-LU-1 cells was thermally deactivated as described in Example 3.

The results are shown below.

| Sample/Control | Ct | Results |
|---|---|---|
| 10 cells | 29.71 | Negative |
| 100 cells | 28.98 | Negative |
| $10^3$ cells | 29.18 | Negative |
| $10^4$ cells | 29.73 | Negative |
| $10^5$ cells | 29.24 | Negative |
| Negative control | 29.68 | Negative |
| Positive control | 20.11 | Positive |
| Thermally deactivated lysate supernatant | 29.93 | Negative |

The $10-10^5$ SK-LU-1 cells are all telomerase negative as detected by WATA, further confirming the specificity of the WATA method for detecting the telomerase activity.

Example 12: Effect of the WATA Method with a TaqMan Probe Substituting for SYBR Green I on Detection of the Telomerase Activity The primer and probe sequence, the reaction tube, the lysis buffer T, the reaction solution T, and the RE/PCR system were the same as those in Example 1. In the RE/PCR system, the SYBR green I was replaced by 0.5 μmol/L TaqMan probe (having a sequence of 5'-FAM-TAAC-CCTAACCCTAACCCTAACCCTAACCC-TAMRA-3'). The cells were A549 cells. The detection method were as described in Example 3. The FAM fluorescent quantitative assay was used in place of the SYBR green I assay. When the Ct value was ≤30, a positive result was determined, and when the Ct value was >30, a negative result was determined.

The result is shown below.

| Sample | Ct | Results |
|---|---|---|
| Lysis buffer | No Ct | Negative |
| 10 cells | 29.82 | Positive |
| 100 cells | 25.37 | Positive |
| 1000 cells | 22.15 | Positive |
| 10000 cells | 18.61 | Positive |
| Thermally deactivated lysate supernatant | 33.54 | Negative |

It can be seen that the telomerase activity in 10-10000 A549 cells can be detected by the WATA method using TaqMan.

What is claimed is:

1. A method for detecting telomerase activity by washing-free, anchored-extension and telomeric-binding amplification comprising:
   adding a cell lysate supernatant of a sample to be tested to a PCR tube with a telomerase primer fixed thereto;
   placing the PCR tube on ice to bind telomerase to the telomerase primer;
   aspirating off the cell lysate supernatant from the PCR tube, adding to the PCR tube a telomerase reaction system and then incubating the PCR tube at 30-37° C. to perform a telomeric G sequence extension reaction;
   incubating the PCR tube at 55-65° C. to perform a hybridization reaction;
   aspirating off supernatant from the PCR tube, adding to the PCR tube a PCR reaction solution containing a restriction endonuclease and PCR primers, and incubating the PCR tube at 37° C. for 10 min; and
   carrying out a PCR reaction to be analyzed for detection of the telomerase activity, wherein the telomerase primer has a sequence of:

```
                                                (SEQ ID NO: 1)
   5'-TCCGTCGAGCAGAGTTAGGGTTAG-3',
   ``` and the PCR primers are:

```
                                                (SEQ ID NO: 4)
   5'-CCGTCACCCTGGATGCTGTAGG-3',
   and
                                                (SEQ ID NO: 5)
   5'-AAGAGCCGCGAGCGATCCTT-3'.
   ```

2. The method of claim 1, wherein the method further comprises:
   (1) synthesizing the telomerase primer and fixing the telomerase primer to the PCR tube;
   (2) synthesizing a template probe and an inhibitory probe, respectively;

(3) complexing the template probe and the inhibitory probe to form a double-stranded DNA designated as dsTU;
(4) adding a lysis buffer to the sample to be tested to form a mixture, and repeatedly pipetting the mixture, and then transferring the mixture to a centrifuge tube;
(5) placing the centrifuge tube on ice for 10 min, and centrifuging the centrifuge tube at 4° C. to obtain supernatant to be used as a lysate supernatant;
(6) adding the lysate supernatant to the PCR tube, placing the PCR tube on ice for 30 min;
(7) aspirating off liquid in the PCR tube, thereafter adding to the PCR tube a telomerase reaction solution, and then incubating the PCR tube at 30-37° C. for 30-60 min and at 55-65° C. for 15-30 min;
(8) aspirating off liquid in the anchor PCR tube, thereafter adding to the PCR tube a restriction endonuclease/PCR reaction solution, and then performing a PCR reaction,
wherein the template probe has a sequence of:

(SEQ ID NO: 2)
5'-CCGTCACCCTGGATGCTGTAGGATCCCTAACCCTAACCCTAACCCTA
ACCCTAACCCTAAGGATCGCTCGCGGCTCTT-3', the inhibitory probe sequence has a sequence of:

(SEQ ID NO: 3)
5'-TAGGGTTAGGGATCCTACA-3'.

3. The method of claim 2, wherein the telomerase reaction solution in Step (7) has a composition of: 0.06 mmol/L of dNTP, 1 nmol/L of dsTU, 1.5 mmol/L of $MgCl_2$, 63 mmol/L of KCl, 1 mmol/L of EGTA-Na, 0.1 mg/ml of BSA, 0.05% of Tween 20, and 20 mmol/L of Tris-HCl with pH 8.0 as a solvent.

4. The method of claim 2, wherein the restriction endonuclease/PCR reaction solution in Step (8) has a composition of: 0.2 mmol/L of dNTP, 1 U/50 µl of Taq enzyme, 0.2 µmol/L of PCR primer, 0.4×SYBR Green I, 2 U/50 µl of BamHI, 50 mmol/L of KCl, 1.5 mmol/L of $MgCl_2$, 0.05% of Tween 20, and 10 mmol/L of Tris-HCl with pH 9.0 as a solvent.

5. A kit for detecting telomerase activity by washing-free, anchored-extension and telomeric-binding amplification, comprising an anchor PCR tube fixed with a telomerase primer, a template probe, an inhibitory probe, PCR primers, a telomerase reaction buffer, a restriction endonuclease/PCR reaction buffer, a Taq enzyme and a BamHI enzyme,
wherein the telomerase primer has a sequence of:

(SEQ ID NO: 1)
5'-TCCGTCGAGCAGAGTTAGGGTTAG-3';

the template probe has a sequence of:

(SEQ ID NO: 2)
5'-CCGTCACCCTGGATGCTGTAGGATCCCTAACCCTAACCCTAACCCTA
ACCCTAACCCTAAGGATCGCTCGCGGCTCTT-3', the inhibitory probe has a sequence of:

(SEQ ID NO: 3)
5'-TAGGGTTAGGGATCCTACA-3', the PCR primers are:

(SEQ ID NO: 4)
5'-CCGTCACCCTGGATGCTGTAGG-3',
and (SEQ ID NO: 5)
5'-AAGAGCCGCGAGCGATCCTT-3'.

6. The kit of claim 5, wherein the kit further comprises a cell lysis buffer with a composition of: 1 mmol/L of $MgCl_2$, 1 mmol/L of EGTA-Na, 1% of NP-40, 0.25 mmol/L of sodium deoxycholate, 150 mmol/L of NaCl, 10% of glycerol, 5 mmol/L of 2-mercaptoethanol, 0.1 mmol/L of AEBSF, and 10 mmol/L of Tris-HCl with pH 7.5 as a solvent.

* * * * *